(12) United States Patent
Bonnard

(10) Patent No.: US 7,252,802 B2
(45) Date of Patent: Aug. 7, 2007

(54) APPARATUS AND METHOD FOR IGNITING SAMPLE IN CALORIMETERS

(76) Inventor: John Anthony Bonnard, Plot 135, Knoppieslaagte, Centurion, Pretoria, Gauteng (ZA) 0002

( * ) Notice: Subject to any disclaimer, the term of this patent is extended or adjusted under 35 U.S.C. 154(b) by 766 days.

(21) Appl. No.: 10/204,062

(22) PCT Filed: Feb. 19, 2001

(86) PCT No.: PCT/ZA01/00020

§ 371 (c)(1), (2), (4) Date: Aug. 16, 2002

(87) PCT Pub. No.: WO01/61327

PCT Pub. Date: Aug. 23, 2001

(65) Prior Publication Data

US 2003/0012251 A1    Jan. 16, 2003

(30) Foreign Application Priority Data

Feb. 18, 2000    (ZA) ................................. 2000/0794

(51) Int. Cl.
*G01N 30/00*    (2006.01)
(52) U.S. Cl. ......................... 422/51; 422/102; 422/107
(58) Field of Classification Search ................. 422/50, 422/51, 68.1, 78, 102
See application file for complete search history.

(56) References Cited

U.S. PATENT DOCUMENTS

| | | | |
|---|---|---|---|
| 1,289,918 A | 12/1918 | Roehrich | |
| 1,708,873 A | 4/1929 | Darroch | |
| 3,368,401 A | 2/1968 | Beauxis, Jr. | |
| 3,451,267 A | 6/1969 | Wiegert et al. | |
| 4,616,938 A | 10/1986 | Bonnard | |
| 4,925,315 A | 5/1990 | Bonnard | |

FOREIGN PATENT DOCUMENTS

| | | |
|---|---|---|
| GB | 2089507 | 6/1982 |
| JP | 05052675 | 3/1993 |
| JP | 06034462 | 2/1994 |
| JP | 07270258 | * 10/1995 |
| JP | 06034452 | * 2/1999 |

* cited by examiner

*Primary Examiner*—Jill Warden
*Assistant Examiner*—Samuel P. Siefke
(74) *Attorney, Agent, or Firm*—Keusey, Tutunjian & Bitetto, P.C.

(57) ABSTRACT

An apparatus and method for igniting a sample in a calorimeter. A heating element is used to ignite a solid or liquid substance inside the calorimeter, and the burning substance is allowed to move into contact with a sample in a crucible to ignite the sample.

12 Claims, 2 Drawing Sheets

APPARATUS AND METHOD FOR IGNITING SAMPLE IN CALORIMETERS

BACKGROUND OF THE INVENTION

1. Field of the Invention

The invention relates to calorimeters, and more particularly, relates to the ignition of a sample within a calorimeter.

2. Related Art

A sample material which is to be tested in a calorimeter is normally ignited using one of two methods.

In the first instance use is made of a length of resistance or fuse wire which is positioned so that it contacts a sample material which is in a calorimeter and which is to be ignited. An electric current is passed through the wire which is thereby heated to a temperature which causes ignition of the sample material. Although this technique works satisfactorily the resistance wire has a short life time and, in some applications, must be replaced after the combustion of each sample material.

It is also known to make use of a combustible thread such as cotton which is brought into contact with, or positioned so that it extends into, the sample material. A portion of the thread is attached to a resistance or fuse wire which is heated by passing an electrical current through the wire. When the temperature of the wire is increased sufficiently the thread is ignited and burns along its length and the flame ignites the sample material once the flame reaches the sample material. Again this process works satisfactorily but it suffers from the drawback that a correctly positioned fresh thread must be inserted into the calorimeter each time a sample is to be ignited.

Many calorimeters have been automated so that practically all the required steps in a calorimetric measurement are automatically carried out in the correct sequence. The problem associated with igniting the sample material, ie. the repeated replacement of the resistance wire or combustible thread, as the case may be, has however mitigated against the implementation of a completely automated process.

SUMMARY OF THE INVENTION

The invention provides apparatus for igniting a sample in a calorimeter which includes a heating device, holder means for placing a combustible substance in contact with or in proximity to the heating device thereby to ignite the substance which, once burnt to a predetermined extent, is movable away from the heating device, and a sample holder which is positioned to receive the burning substance as it moves away from the heating device.

The sample holder may be of any appropriate type and preferably is a conventional crucible.

The burning substance may be movable away from the heating device in any appropriate way and preferably is movable under gravity action or, at least initially, under the action of pressure which is generated by the burning substance. In this instance the sample holder, ie. the crucible, is positioned lower than the heating device and is orientated so that a sample on the sample holder will be impacted by the moving burning substance.

The heating device is preferably electrically operated. The heating device may take on any suitable form and for example may include or comprise a filament wire, a resistance wire, or any equivalent device which is heated by the passage of electric current at least to a temperature which is equal to the ignition temperature of the substance.

The holder means may be part of or be formed by the heating device. For example in one form of the invention the heating device includes at least one filament wire shaped to receive the combustible substance. The filament wire may have a loop which is in proximity to, or which receives, the combustible substance and, as the combustible substance is burned, its size diminishes to a point at which the combustible substance is automatically disengaged from the loop. This is given merely by way of a non-limiting example.

In a preferred form of the invention the holder means is a funnel-shaped component in which the combustible substance is located and the heating device is positioned inside the funnel so that the combustible sample, inside the funnel, is automatically brought into contact with, or in proximity to, the heating device.

The funnel may include an outlet which is located above the sample holder with the outlet being sized so that the combustible substance, once reduced in size by burning, can fall through the outlet under the action of gravity onto the sample holder. Alternatively or additionally pressure which is generated by the burning substance exerts a force on the substance which, at least initially, propels the substance towards the sample holder.

The invention also provides a method of igniting a sample in a calorimeter which includes the steps of igniting a combustible substance and allowing the burning substance to move into contact with a sample inside the calorimeter thereby to ignite the sample.

Although the combustible substance may be allowed, or caused, to move in any appropriate way inside the calorimeter, it is preferred that the combustible substance moves under gravity action, ie. falls, or is propelled at least initially by pressure generated by the burning substance, into contact with the sample.

The combustible substance may be liquid or solid. If liquid the combustible substance may be a drop of the liquid which is placed in any appropriate way, for example by injection means in the calorimeter at a location at which it is in contact with, or in proximity to, a suitable heating device.

If the combustible substance is solid then preferably the solid is provided in a granular or pelletised form.

Preferably the combustible substance is caused to ignite by making use of electrical heating means It is important that the combustible substance burns relatively slowly even inside the highly oxygen charged atmosphere which prevails in a calorimeter. Ignition of the combustible substance takes place at a point which is spaced from the sample in the calorimeter and the burning substance, while burning, moves or is caused to move to the sample material so that it reaches the sample while still burning. The combustible substance must therefore burn for a period which is relatively long at least compared to the combustion period of thread or cotton which is conventionally used for igniting a calorimetric sample.

The invention also extends to a combustible substance for use in the apparatus or method of the invention. The combustible substance may be liquid or solid.

In the former instance the combustible liquid may be formed from a mixture of at least two components such as water and alcohol. The ratio of water to alcohol is adjusted according to the particular circumstances in the calorimeter, and the drop size of the liquid, to ensure that a falling liquid drop is not fully consumed by the ignition process before the drop impacts on the sample.

If the combustible substance is solid then it is preferably provided in granular or pelletised form A suitable substance is for example a mixture of benzoic acid and alumina powder.

The invention is however not limited in the nature or type of combustible substance which can be used provided only that the combustible substance, once ignited, will burn for a period which is sufficiently long to ensure that the burning substance impacts the sample in the calorimeter

BRIEF DESCRIPTION OF THE DRAWINGS

The invention is further described by way of examples with reference to the accompanying drawings in which.

DESCRIPTION OF PREFERRED EMBODIMENTS

Figure 1:
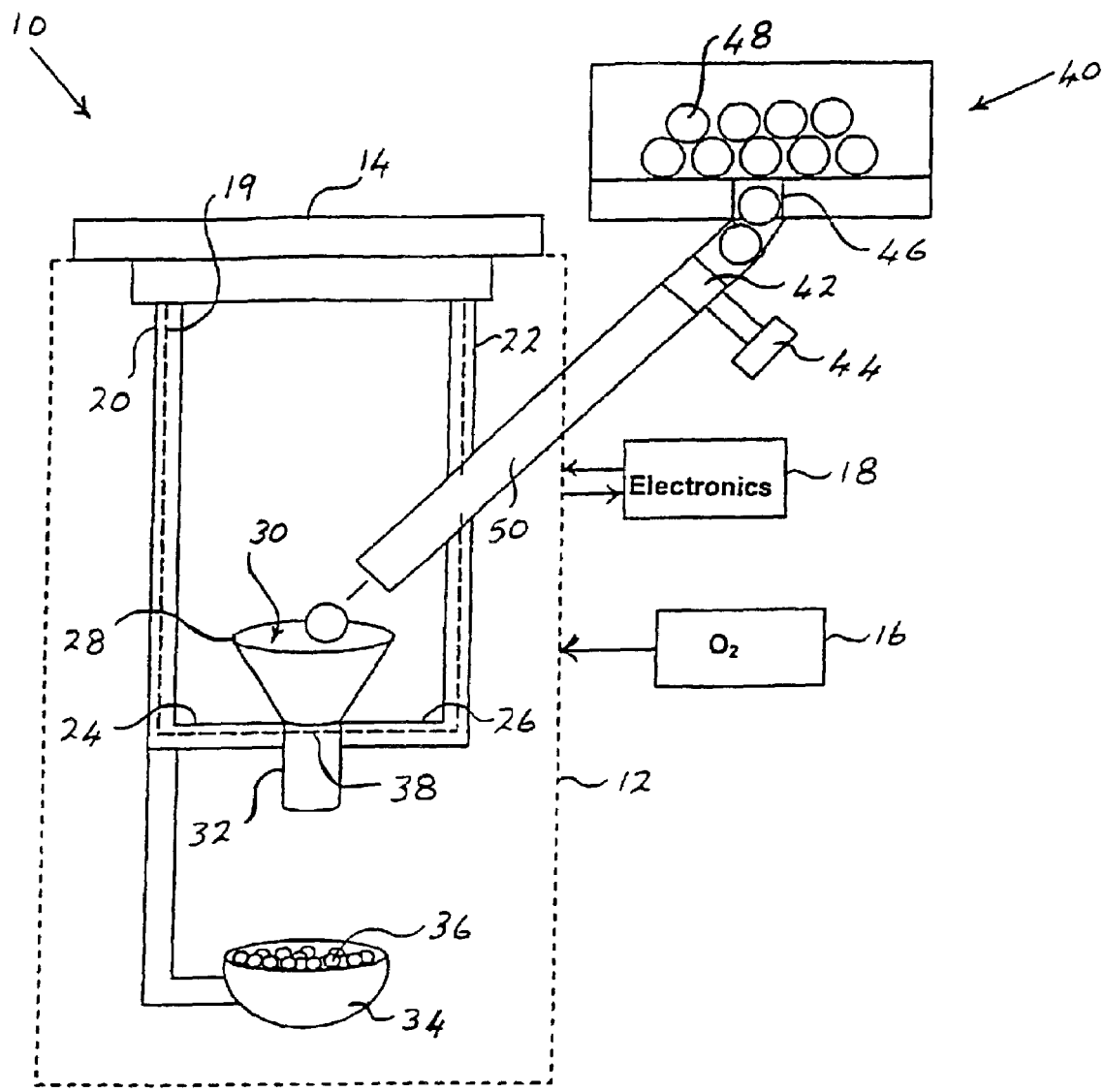
FIG. 1 is a schematic side view of a calorimeter wherein a sample is ignited in accordance with the principles of the invention.

FIG. 1 of the accompanying drawings illustrates, somewhat schematically and from the side, a portion of a calorimeter 10 wherein a sample is ignited in accordance with the principles of the invention.

FIG. 1 schematically depicts only that part of a calorimeter bomb which is necessary for an understanding of the invention. Generally the bomb is constructed in a conventional manner and, for this reason, is only shown notionally by means of dotted lines 12 and not further described herein. The calorimeter includes a removable lid 14. Oxygen from a suitable source 16 can be charged into the interior of the bomb. A conventional electronic control system, schematically represented by a block 18, which includes temperature sensors and the like, is provided for operating, and monitoring the operation of, the bomb. Again no novelty is claimed in respect of these components and, for this reason, as is the case of the oxygen charging system, no further description is included in this specification.

Inside the bomb and supported in any appropriate manner or by structure of the bomb, are two spaced support members 20 and 22 respectively. These members are for example made from a heat resisting material such as stainless steel and include internal electrical conductors, indicated schematically by dotted lines 19, which lead from the electronic system 18 to electrodes 24 and 26 which extend towards one another from the respective members 20 and 22.

A funnel-shaped holder 28, which is made from a suitable heat resisting material, is supported by the electrodes at a central position inside the bomb. A mouth 30 of the funnel faces upwardly and a discharge spout 32 of the funnel faces downwardly and is directly positioned over a crucible 34 which is of known construction and which is suitably supported The crucible, in use of the calorimeter, receives a sample 36 of material which is to be tested.

As has been indicated in the preamble of this specification many calorimeters have been developed to the point at which they are substantially completely automated in operation. Thus the placing of a sample in the crucible, the closure of the bomb, the charging of the bomb with oxygen, the ignition of the sample and the monitoring of the subsequent reactions, and any other steps save for preliminary work required to ignite the sample, can all be automated and carried out automatically in the correct sequence.

A filament wire 38 of a relatively robust construction is positioned inside the conical holder 28 so that it traverses the outlet 32, effectively reducing the cross sectional area of the outlet, and is connected to and between the electrodes 24 and 26.

A dispensing device 40 is positioned outside the bomb at any appropriate location which depends, at least, on the nature of the dispensing device. Any appropriate dispensing device can be used. In this instance a housing of the dispensing device includes a door 42 which is movable by means of an actuator 44 under the control of the electronic unit 18. The door 42 is movable between a first position at which it exposes an opening 46 in the housing of the dispenser and a second position at which the opening is totally sealed. The arrangement is such that the door, when moved by the actuator, is opened and then closed thereby to allow one pellet 48, from a plurality of pellets in the housing of the device 40, to be discharged through the opening. The pellet then falls under gravity action and is guided inside a chute 50 thereby to fall directly into the funnel-shaped holder 28. The door is designed so that when it closes the opening 46 it simultaneously effectively seals the opening in a gas-tight manner which is well able to withstand the working requirements of the calorimeter.

In this example of the invention each pellet 48 is made to a predetermined size from suitable ingredients. For example the pellets may be formed from a precisely formed mixture of benzoic acid and alumina powder which is pelletised and which is then formed into a plurality of pellets, each pellet being of an exact size eg. approximately 0.5 mm in diameter, and hence of an exact weight. The pellets should be as small as possible to limit extraneous effects produced in the bomb by the ignition of the pellets.

As has been noted the dispenser 40 causes one of the pellets 48 to be passed through the opening 46 into the holder 28. The important aspect about this step is that it can be carried out totally automatically. In a preferred form of the invention all of the remaining steps in the calorimetric process are also carried out automatically. Thus the sample 36 is placed in the crucible 34 and the bomb is closed and charged with oxygen The electronic unit then applies a voltage to the electrodes 24 and 26 which causes a current of a predetermined magnitude to flow through the filament wire 38 for a predetermined period. The pellet 48 which is in the holder initially rests on the filament wire 38. The filament wire, when heated to the required extent, caused the pellet 48 to be ignited. The pellet commences burning, although it burns relatively slowly due to its composition and structure. Ultimately however the pellet is reduced in size sufficiently so that it can fall under gravity action past the filament 38 and through the outlet spout 32. The pellet continues burning as it falls through the oxygen in the bomb onto the sample in the crucible. The burning pellet, when it impacts the sample, almost instantaneously causes ignition of the sample so that the calorimetric measuring process can be completed.

The crux of the invention is that the combustible substance constituted by the pellet is ignited and the pellet is then caused or allowed to migrate, while burning, by gravity or other action, onto or near the sample material under test in the calorimeter thereby causing the sample material to ignited.

Figure 2:
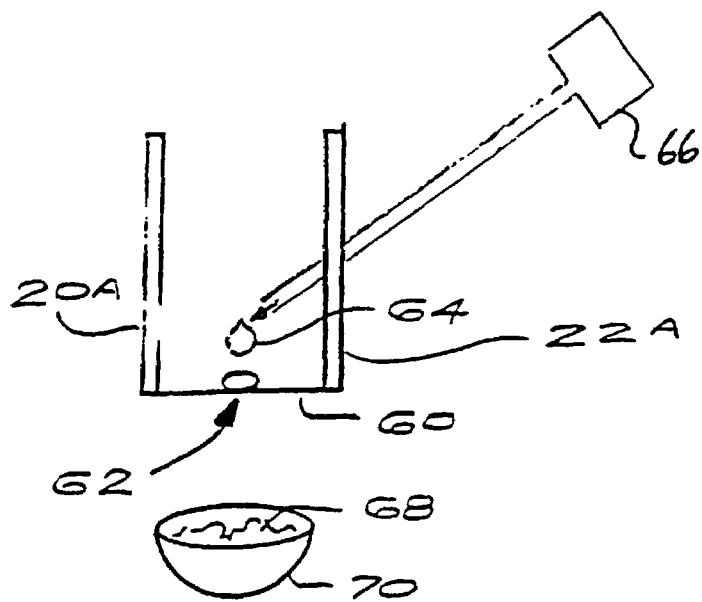
FIGS. 2 and 3 illustrate possible variations of the apparatus of the invention.
Figure 3:
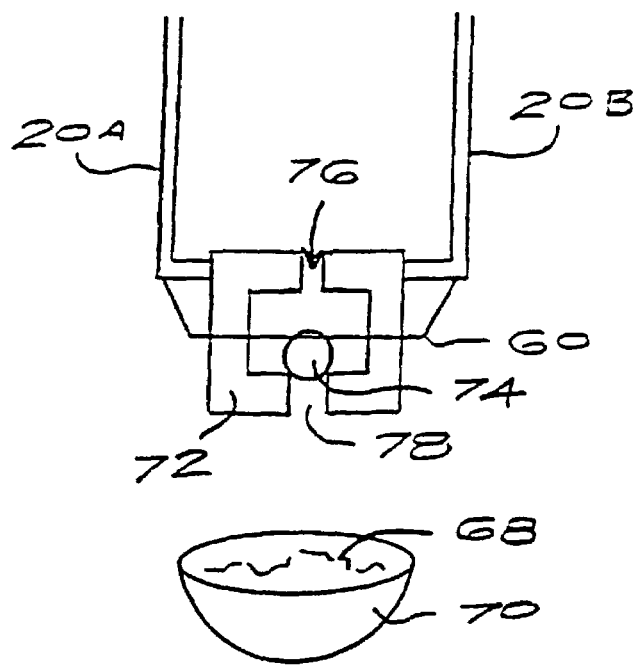

The aforementioned principle can be used in other ways to cause ignition of the sample material FIGS. 2 and 3, illustrate, somewhat conceptually, two variations of the invention. In the former instance a filament wire 60 is bent with a central loop 62 and is supported between extremities of spaced members 20A and 22A which are similar to the members 20 and 22 respectively in FIG. 1. A dispenser places a combustible substance 64 on the loop The combustible substance could be a pellet of the type described in connection with FIG. 1 Alternatively it could be a drop of a combustible liquid such as a mixture of alcohol and water which is made to a suitable ratio of ingredients and which is then placed, for example by means of a drop injection mechanism 66, of any appropriate construction, directly onto the loop 62. The mechanism 66 is of a type known in the art, and no novelty is claimed in respect thereof. When activated it produces a single droplet of the combustible liquid mixture which is directed onto the loop 62. The liquid adheres, due to capillary action or surface tension effects, to the loop 62. When the filament wire is heated by passing a current through the wire the loop 62 heats the liquid drop which adheres to the loop and the drop is ignited and burns, again relatively slowly, until its size is reduced to such an extent that the drops falls through the loop under gravity action directly onto a sample 68 contained in an underlying crucible 70. The sample is thereby ignited.

The combustible drop 64 is sufficiently small eg. again of the order of 0.5 mm in diameter, a size which is similar to the diameter of the loop 62, to ensure that initially the drop adheres to the loop. Also the amount of energy released into the bomb by ignition of the drop is small.

In the arrangement shown in FIG. 3 like reference numerals designate like components. The filament wire 60 is not bent to form a loop but instead directly traverses a space between walls of a holder 72 which is supported by the members 20A and 20B. A combustible drop 74, eg of water and alcohol, is introduced into the interior of a housing of the holder through an inlet or upper opening 76 and comes to rest on lower inner surfaces of the holder adjacent an outlet 78 from the holder. When the filament wire is heated by the application of an electric current the drop is ignited and once it has burnt to some extent the pressure which is built up inside the holder by this combustion causes the remainder of the drop to be ejected through the outlet 78 onto a sample 68 in an underlying crucible 70 Again it is to be noted, with FIGS. 2 and 3, that the invention makes use of a separate substance which is ignited and, while burning, is allowed to move through the interior of the bomb into contact with the sample material which is then caused to ignite.

Clearly the principles of the invention can be used in ways other than those described in connection with FIGS. 1 to 3 and such variations are intended to fall within the scope of the present invention.

The invention claimed is:

1. An apparatus for igniting a sample in a calorimeter comprising:
   a crucible for receiving the sample;
   a heating device;
   holder means for placing a combustible substance in contact with or in proximity to said heating device in order to ignite the substance, wherein when the substance is burnt to a predetermined extent, it is movable away from the heating device to the crucible, said holder means comprises a funnel-shaped component having said heating device positioned therein, wherein when said combustible substance is disposed inside the funnel, it is automatically brought into contact with, or in proximity to, said heating device; and
   wherein the crucible is positioned to receive the burning combustible substance as it moves away from the heating device so that the sample is thereby ignited by the burning combustible substance.

2. The apparatus according to claim 1, wherein said heating device is heated by the passage of electric current to a temperature which is at least equal to an ignition temperature of the combustible substance.

3. The apparatus according to claim 1, wherein said heating device includes at least one filament wire shaped to receive the combustible substance.

4. The apparatus according to claim 1, wherein said funnel includes an outlet located above said crucible and being sized so that said combustible substance, once reduced in size by burning, can fall through the outlet under the action of gravity into said crucible.

5. An apparatus for igniting a sample in a calorimeter comprising:
   a crucible for receiving the sample;
   a heating device;
   holder means for placing a combustible substance in contact with or in proximity to said heating device in order to ignite the substance, wherein when the substance is burnt to a predetermined extent, it is movable away from the heating device to the crucible, in said holder means comprises a housing having an inlet, an interior and an outlet, the combustible substance being introduced to said interior through said inlet, wherein the burning combustible substance is ejected from said outlet after ignition by said heating device, and wherein the crucible is positioned to received the burning combustible substance as it moves away from the heating device do that the sample is thereby ignited by the burning combustible substance.

6. The apparatus according to claim 1, wherein the combustible substance comprises a granular mixture of benzoic acid and alumina powder.

7. The apparatus according to claim 1, wherein the combustible substance comprises a pelletised mixture of benzoic acid and alumina powder.

8. The apparatus according to claim 5, wherein said heating device is heated by the passage of electric current to a temperature which is at least equal to an ignition temperature of the combustible substance.

9. The apparatus according to claim 5, wherein said heating device includes at least one filament wire shaped to receive the combustible substance.

10. The apparatus according to claim 5, wherein the combustible substance comprises a granular mixture of benzoic acid and alumina powder.

11. The apparatus according to claim 5, wherein the combustible substance comprises a pelletised mixture of benzoic acid and alumina powder.

12. The apparatus according to claim 5, wherein said heating device is at least partially housed within the housing thereby at least partly protecting the heating device from the heat of combustion of the sample.

* * * * *

UNITED STATES PATENT AND TRADEMARK OFFICE
CERTIFICATE OF CORRECTION

PATENT NO. : 7,252,802 B2  Page 1 of 1
APPLICATION NO. : 10/204062
DATED : August 7, 2007
INVENTOR(S) : John Anthony Bonnard It is certified that error appears in the above-identified patent and that said Letters Patent is hereby corrected as shown below:

Column 6, claim 5, line 27, delete "in" between "crucible," and "said"
Column 6, claim 5, line 35, change "do" to --so-- between "device" and "that"

Signed and Sealed this

Twenty-third Day of October, 2007

JON W. DUDAS
*Director of the United States Patent and Trademark Office*